(12) United States Patent
Likitlersuang et al.

(10) Patent No.: US 9,078,854 B2
(45) Date of Patent: *Jul. 14, 2015

(54) PRESERVATIVE FREE BIMATOPROST AND TIMOLOL SOLUTIONS

(75) Inventors: Sukhon Likitlersuang, Anaheim, CA (US); Ajay Parashar, Irvine, CA (US); Chetan P. Pujara, Irvine, CA (US); William F. Kelly, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 13/812,597

(22) PCT Filed: Jul. 28, 2011

(86) PCT No.: PCT/US2011/045654
§ 371 (c)(1),
(2), (4) Date: May 30, 2013

(87) PCT Pub. No.: WO2012/015998
PCT Pub. Date: Feb. 2, 2012

(65) Prior Publication Data
US 2014/0148455 A1    May 29, 2014

Related U.S. Application Data

(60) Provisional application No. 61/368,685, filed on Jul. 29, 2010.

(51) Int. Cl.
| | |
|---|---|
| A61K 31/5575 | (2006.01) |
| A61K 31/5377 | (2006.01) |
| A61K 31/165 | (2006.01) |
| A61K 9/00 | (2006.01) |
| A61K 9/08 | (2006.01) |
| A61K 47/02 | (2006.01) |
| A61K 47/12 | (2006.01) |

(52) U.S. Cl.
CPC ............ *A61K 31/165* (2013.01); *A61K 9/0048* (2013.01); *A61K 9/08* (2013.01); *A61K 31/5377* (2013.01); *A61K 31/5575* (2013.01); *A61K 47/02* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 4,494,274 A | 1/1985 | Thurlow | |
| 4,599,353 A | 7/1986 | Bito | |
| 4,994,274 A | 2/1991 | Chan | |
| 5,028,624 A | 7/1991 | Chan | |
| 5,034,413 A | 7/1991 | Chan et al. | |
| 5,268,624 A | 12/1993 | Zanger et al. | |
| 5,688,819 A * | 11/1997 | Woodward et al. | 514/357 |
| 6,051,576 A | 4/2000 | Ashton et al. | |
| 6,184,250 B1 | 2/2001 | Klimko | |
| 6,248,735 B1 | 6/2001 | Baldwin et al. | |
| 8,309,605 B2 * | 11/2012 | Chang et al. | 514/530 |
| 2004/0082660 A1 | 4/2004 | Ueno | |
| 2010/0210720 A1 * | 8/2010 | Pilotaz et al. | 514/530 |

FOREIGN PATENT DOCUMENTS

| | | |
|---|---|---|
| EP | 0286903 | 10/1988 |
| EP | 0364417 | 4/1990 |
| EP | 0458590 | 11/1991 |
| EP | 0509752 | 10/1992 |
| EP | 0590972 | 4/1994 |
| EP | 1057486 | 6/2000 |
| EP | 0660716 | 11/2001 |
| EP | 2127638 | 12/2009 |
| FR | 2918891 * | 1/2009 |
| WO | 97-30710 | 8/1997 |
| WO | 98-25620 | 6/1998 |
| WO | 00-04898 | 2/2000 |
| WO | 00-054810 | 9/2000 |
| WO | 02-092098 | 11/2002 |
| WO | 2007-042262 | 4/2007 |

OTHER PUBLICATIONS

U.S. Appl. No. 13/785,911, filed Mar. 2013, Likitlersuang et al.*
Ganfort® 0.3-5 Eye Drops, May 2009.*
Lumigan™ Package Insert, NDA 21-275, Mar. 2001.*
Jaenen, N. et al, Ocular Symptoms and Signs with Preserved and Preservative-Free Glaucoma Medications, European Journal of Ophthalmology, 2007, 341-349, 17(3).
Leung, Eamon et al, Prevalence of Ocular Surface Disease in Glaucoma Patients, J Glaucoma, 2008, 350-355, 17.
Liang, Hong et al, Comparison of the Ocular Tolerability of a Latanoprost Cationic Emulsion Versus Conventional Formulations of Prostaglandins: An in Vivo Toxicity Assay, Molecular Vision, 2009, 1690-1699, 15.
Lumigan Package Insert, Mar. 2001, 6 Pages, NDA 21-275.
Alexander, Christy et al, Prostaglandin Analog Treatment of Glaucoma and ocular Hypertension, Ann Pharmacother, 2002, 504-511, 35.
Ashton, Paul et al, Formulation Influence on Conjunctival Penetration of Four Beta Blockers in the Pigmented Rabbit: A Comparison with Corneal Penetration, Pharmaceutical Research, 1991, 1166-1174, 8 (9).
Bean, Gerald, Commercially Available Prostaglandin Analogs for the Reduction of Intraocular Pressure: Similarities and Differences, Survey of Ophthalmology, 2008, S69-S84, 53 (Supp. 1).
Bito, Esterified Prostaglandin Shows 'Potent' Promise, Pharmacology Prodrugs, 1989, 2 Pages, 5.
Bito, LZ, Biological Protection with Prostanoids, CRC Press, Inc., 1985, 231-252, 1, Cohen, M. M., ed., Boca Raton, Fla.
Bito, LZ, Prostaglandins, Old Concepts and New Perspectives, Archives of Ophthalmology, 1987, 1036-1039, 105.
Bito, LZ, Prostaglandins, Other Eicosanoids, and Their derivatives as Potential Antiglaucoma Agents, Glaucoma: Applied Pharmacology, 1984, 477-505, 20.

(Continued)

*Primary Examiner* — Svetlana M Ivanova
(74) *Attorney, Agent, or Firm* — Lorenz Siddiqi

(57) ABSTRACT

The present invention is directed to preservative-free solutions of bimatoprost and timolol for lowering intra-ocular pressure and treatment of glaucoma.

8 Claims, No Drawings

(56) References Cited

OTHER PUBLICATIONS

Calissendorff, Berit et al, Bioavailability in the Human Eye of a Fixed Combination of Latanoprost and Timolol Compared to Monotherapy, Journal of Ocular Pharmacology and Therapeutics, 2002, 127-131, 18(2).
Campbell, S.H. et al, Double-Masked Three-Period Crossover Investigation of Timolol in Control of Raised Intraocular Pressure, Eye, 1993, 105-108, 7.
Cantor, Louis et al, Bimatoprost: A Member of a New Class of Agents, the Prostamides, for Glaucoma Management, Exp. Opin. Invest. Drugs, 2001, 721-731, 10 (4).
Chiou, G.C., Development of D-Timolol for the Treatment of Glaucoma and Ocular Hypertension, J. Ocul. Pharmacol., 1990, 67-74, 6 (1).
Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).
Eisenberg, Dan, Bimatoprost and Travoprost: A Review of Recent Studies of Two New Glaucoma Drugs, Survey of Ophthalmology, 2002, S105-S115, 47 (1).
Heijl, Anders et al, Reduction of Intraocular Pressure and Glaucoma Progression: Results From the Early Manifest Glaucoma Trial, Arch Ophthalmol, 2002, 1268-1279, 120.
Hommer, A., Bimatoprost: Erste Wirksubstanz Einer Neuen Stoffklasse, Der Prostamide Fur Die Glaukombehandlung, Spektrum Augenheilkd, 2001, 146-149, 15.
Kass, Michael et al, The Ocular Hypertension Treatment Study: A Randomized Trial Determines That Topical Ocular Hypotensive Medication Delays or Prevents the Onset of Primary Open-Angle Glaucoma, Arch. Ophthalmol., 2002, 701-713, 120.
Komoto, Junichi, Prostaglandin F2α Formation From Prostaglandin H2 by Prostaglandin F Synthase (PGFS): Crystal Stucture of PGFS Containing Bimatoprost, American Chemical Society, Feb. 21, 2006, 1987-1996, 45 (7).
Krauss, Achim, Update on the Mechanism of Action of Bimatoprost: A Review and Discussion of New Evidence, Surv. Ophthalmol., 2004, S5-S11, 49 (Supp. 1).
Laibovitz, Robert, Comparison of the Ocular Hypotensive Lipid AGN 192024 With Timolol, Arch Ophthal, 2001, 994, 119.
Larsson, Lil-Inger, The Effect on Diurnal Intraocular Pressure of the Fixed Combination of Latanoprost 0.005% and Timolol 0.5% in Patients With Ocular Hypertension, Acta Ophthalmol. Scand., 2001, 125-128, 79.
Leske, Cristina et al, Predictors of Long-Term Progression in the Early Manifest Glaucoma Trial, Ophthalmology, 2007, 1965-1972, 114.
Leske, M. Cristina et al, Factors for Glaucoma Progression and the Effect of Treatment: The Early Manifest Glaucoma Trial, Ophthalmology, 2003, 1965-1972, v114, #11.
Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).
Mills, K.B., Blind Randomised Non-Crossover Long-Term Trial Comparing Topical Timolol 0.25% with Timolol 0.5% in the Treatment of Simple Chronic Glaucoma, British Journal of Ophthalmology, Apr. 1983, 216-219, 67(4).
Nilsson, SIV, PGF 2α Increases Uveoscleral Outflow, Invest. Ophthalmol. Vis. Sci, 1987, 284, 28 (Suppl).
Ota, Takashi, The Effects of Prostaglandin Analogues on IOP in Prostanoid FP-Receptor-Deficient Mice, Invest. Ophthalmol. Vis. Sci., 2005, 4159-4163, 46.
Resul, et al, Structure-Activity Relationships of Prostagladin Analogues as Ocular Hypotensive Agents, Current Opinion in Therapeutic Patents, 1993, 781-795, US.
Sharif, Najam, Bimatoprost (Lumigan ®) is an Agonist at the Cloned Human Ocular FP Prostaglandin Receptor: Real-Time FLIPR-Based Intracellular Ca2+ Mobilization Studies, Prostaglandins, Leukotrienes and Essential Fatty Acids, 2003, 27-33, 68.
Sharif, Najam, Bimatoprost and Its Free Acid Are Prostaglandin FP Receptor Agonists, European Journal of Pharmacology, 2001, 211-213, 432.
Sorbera, L.A., Bimatoprost, Drugs of the Future, 2001, 433-439, 26 (5).
Starr, Michael, Further Studies on the Effects of Prostagladin on Intraocular Pressure in the Rabbit, Exp. Eye Res., 1971, 170-177, 11.
The AGIS Investigators, The Advanced Glaucoma Intervention Study (AGIS): 7. The Relationship Between Control of Intraocular Pressure and Visual Field Deterioration, Am. J. Ophthalmol., 2000, 429-440, 130.
Woodward, David, Pharmacological Characterization of a Novel Antiglaucoma Agent, Bimatoprost (AGN 192024), J. Pharmacol. Exp. Ther., Jan. 24, 2003, 772-785, 305 (2).
Alm, A. et al, Effects of D-Timolol and L-Timolol Eye Drops on Intraocular Pressure and Aqueous Flow. A Dose-Response Study in Normal Eyes. Acta Ophthalmol (Copenh)., Feb. 1990, 19-22, 68(1).
Letchinger, S.L. et al, Can the Concentration of Timolol or the Frequency of Its Administration Be Reduced? Ophthalmology, Aug. 1993, 1259-1262, 100(8).
Stewart, W.C., Timolol Hemihydrate: a New Formulation of Timolol for the Treatment of Glaucoma., J Ocul Pharmacol Ther., Summer 1996, 225-237, 12(2).
Zimmerman, T.J. et al, Timolol Maleate: Efficacy and Safety, Arch Ophthalmol, Apr. 1979, 656-658, 97(4).
European Medicines Agency, European Public Assessment Report Ganfort, Retreived on Oct. 22, 2014 From http://www.emea.europa.eu/humandocs/PDFs/EPAR/ganfort/066806en1.pdf. 3 Pages.

* cited by examiner

PRESERVATIVE FREE BIMATOPROST AND TIMOLOL SOLUTIONS

CROSS REFERENCE TO RELATED APPLICATIONS

This Application is a national phase application under 35 U.S.C. §371 of PCT Patent Application No. PCT/US11/45654, which claims priority to U.S. Provisional Patent Application Ser. No. 61/368,685, which was filed on Jul. 29, 2010, both of which are incorporated herein by reference in their entirety.

FIELD OF THE INVENTION

The present application is directed to preservative-free formulations of bimatoprost and timolol.

BACKGROUND OF THE INVENTION

Bimatoprost is a prostamide, a synthetic analog of prostaglandin $F_{2\alpha}$ ($PGF_{2\alpha}$) with potent ocular hypotensive activity. Bimatoprost lowers intraocular pressure (IOP) in patients with glaucoma or ocular hypertension by increasing outflow of aqueous humor through both the trabecular meshwork and uveoscleral routes. Timolol is a non-selective beta-adrenergic receptor blocker and functions by reducing aqueous humor production through blockage of the beta receptors on ciliary epithelium.

Use of preservative containing eye drops has been implicated in the development or worsening of ocular surface disease. Management of open angle glaucoma and ocular hypertension require long term treatment with eye drops containing preservatives. Symptoms and signs of ocular surface disease such as ocular surface breakdown, irritation, burning, foreign body sensation, dryness, inadequate quantity of tears, etc. are prevalent in a large proportion of patients with open angle glaucoma and ocular hypertension.

Compared to eye drops preserved with benzalkonium chloride, preservative-free eye drops induce significantly fewer ocular symptoms and signs of irritation in patients, such as pain or discomfort, foreign body sensation, stinging or burning, and dry eye sensation.

Patients experiencing hypersensitivity reactions with benzalkonium chloride cannot use a commercial bimatoprost product containing benzalkonium chloride which is preserved even with 0.005% w/v benzalkonium chloride. Benzalkonium chloride also may be absorbed by the soft contact lenses therefore patients wearing soft contact lenses are advised to remove lenses prior to administration and wait at least 15 minutes before reinserting them.

SUMMARY OF THE INVENTION

The present invention is directed to a bimatoprost and timolol solutions without benzalkonium chloride or any other preservative which will be superior from a safety & tolerability standpoint while maintaining and/or improving its efficacy of IOP lowering and be available for use by patients hypersensitive to benzalkonium chloride and be convenient for patients wearing soft contact lenses.

Bimatoprost and timolol ophthalmic solution without preservative is a clear to slightly yellow, isotonic, sterile solution. The drug product contains bimatoprost and timolol as the active ingredients. The inactive ingredients are tonicity and buffer agents, and purified water. Suitable buffers such as sodium phosphate dibasic heptahydrate and citric acid monohydrate and suitable tonicity agents such as sodium chloride may be included. The solution is an aqueous solution having a pH value within the range of about 7 to about 8, and preferably about 7.3. Suitable buffers may be included, such as sodium phosphate dibasic heptahydrate, citric acid monohydrate. Preferably, the tonicity agent such as sodium chloride will be employed in an amount to provide a final osmotic value of at least about 200 mOsm/kg, preferably from about 280 to about 370 mOsm/kg.

The present invention can be made generally according to the teachings of U.S. patent application Ser. No. 10/153,043 which is hereby incorporated by reference in its entirety.

Some embodiments of the invention include the following:

1) A preservative free bimatoprost and timolol composition for lowering intraocular pressure in a human patient comprising the following formulation: about 0.03% w/v bimatoprost; about 0.5% timolol; about 0.268% w/v sodium phosphate dibasic heptahydrate; about 0.014% citric Acid monohydrate; about 0.68% sodium chloride, water, hydrochloric acid, sodium hydroxide and and having a pH of about 7.3.

2) The preservative free bimatoprost and timolol solution of paragraph 1 for lowering intraocular pressure in a human patient comprising the following formulation: 0.03% w/v bimatoprost; 0.5% timolol; 0.268% w/v Sodium Phosphate Dibasic Heptahydrate; 0.014% Citric Acid Monohydrate; about 0.68% sodium chloride, hydrochloric acid, water, sodium hydroxide and having a pH of about 7.3.

3) The preservative free bimatoprost and timolol solution of paragraphs 1-2 wherein the timolol is timolol maleate at 0.68% w/v.

4) A composition as described in Table 1.

5) The bimatoprost and timolol solution of paragraphs 1-4 wherein the solution is useful for treating glaucoma.

6) The bimatoprost and timolol composition of paragraphs 1-4 wherein the composition is a solution wherein the solution is contained in a unit dose kit form.

7) The bimatoprost and timolol composition of any of paragraphs 1-6 wherein the composition is applied once a day to each eye.

8) The bimatoprost and timolol composition of any of paragraphs 1-6 wherein the composition is applied twice a day to each eye.

9) The bimatoprost and timolol compositions of paragraphs 1-4 wherein the composition has greater efficacy with fewer side-effects than bimatoprost and timolol preserved with benzalkonium chloride or another preservative.

10) The composition of paragraph 1 wherein the composition may be a solution, emulsion, dispersion, suspension, reverse emulsion and microemulsion.

11) The composition of paragraph 1 wherein the composition is contained in a unit-dose vial.

12) The composition of paragraph 1 wherein the composition is contained in a multi-dose vial which has antipreservative properties such as metal-ions imbedded in its dispensing tip.

13) The composition of paragraph 12 wherein the metal ions are silver ions.

DETAILED DESCRIPTION OF THE INVENTION

A bimatoprost and timolol ophthalmic formulation of the present invention without preservative is shown in Table-1.

TABLE 1

Example of bimatoprost and timolol ophthalmic solution without preservative according to the present invention:

| Ingredients | Units | Grade | Amount |
|---|---|---|---|
| Bimatoprost | % w/v | N/A | 0.03 |
| Timolol Maleate | % w/v | US P/Ph Eur | 0.68 |
| Sodium Phosphate Dibasic Heptahydrate | % w/v | USP | 0.268 |
| Citric Acid Monohydrate | % w/v | US P/Ph Eur | 0.014 |
| Sodium Chloride | % w/v | US P/Ph Eur | 0.68 |
| Hydrochloric Acid | % w/v | US P/Ph Eur | pH 7.3 |
| Sodium Hydroxide | % w/v | US P/Ph Eur | pH 7.3 |
| Purified Water/WFI | Q.S. | US P/Ph Eur | QS |

The present invention is directed to formulations of bimatoprost and timolol without benzalkonium chloride as a preservative and may be marketed in unit dose form. As a result of the removal of benzalkonium chloride, the present invention results in the same as or greater efficacy without the unwanted side-effects associated with the preservative benzalkonium chloride such as hyperemia, which will improve efficacy of the product in lowering IOP per dosage unit, with superior patient compliance and fewer side-effects. Other side effects which may be avoided with the preservative free compositions of the present invention include, blepharitis, corneal erosion, depression, epiphora, eye discharge, eye dryness, eye irritation, eye pain, eyelid edema, eyelid erythema, eyelid pruritus, foreign body sensation, headache, hypertension, oral dryness, somnolence, superficial punctate keratitis, and visual disturbance.

The invention claimed is:

1. A preservative free bimatoprost and timolol composition for lowering intraocular pressure in a patient comprising the following formulation: about 0.03% w/v bimatoprost; about 0.5% w/v timolol; about 0.268% w/v sodium phosphate dibasic heptahydrate; about 0.014% w/v citric acid monohydrate; about 0.68% w/v sodium chloride; water and having a pH of about 7.3; wherein the composition has better intraocular pressure lowering ability than the same composition preserved with benzalkonium chloride.

2. The preservative free bimatoprost and timolol composition of claim 1 for lowering intraocular pressure in a patient comprising the following formulation: 0.03% w/v bimatoprost; 0.5% w/v timolol; 0.268% w/v sodium phosphate dibasic heptahydrate; 0.014% w/v citric acid monohydrate; 0.68% w/v sodium chloride; water and having a pH of about 7.3.

3. The preservative free bimatoprost and timolol solution of claim 2 wherein the timolol is timolol maleate at 0.68% w/v.

4. The bimatoprost and timolol composition of claim 1 wherein the composition is a solution and is useful for treating glaucoma.

5. The bimatoprost and timolol composition of claim 1 wherein the composition is contained in a unit dose kit form.

6. The bimatoprost and timolol composition of claim 1 wherein the composition is applied once a day to each eye.

7. The bimatoprost and timolol composition of claim 1 wherein the composition is applied twice a day to each eye.

8. The bimatoprost and timolol composition of claim 1 wherein the composition is a solution contained in a unit dose vial.

* * * * *

UNITED STATES PATENT AND TRADEMARK OFFICE
CERTIFICATE OF CORRECTION

PATENT NO. : 9,078,854 B2
APPLICATION NO. : 13/812597
DATED : July 14, 2015
INVENTOR(S) : Sukhon Likitlersuang et al.

Page 1 of 1

It is certified that error appears in the above-identified patent and that said Letters Patent is hereby corrected as shown below:

Title Page, item (56)

On the Page 2, in column 1, under "Other Publications", line 31, delete "Stucture" and insert -- Structure --, therefor.

On the Page 2, in column 2, under "Other Publications", line 13, delete "Prostagladin" and insert -- Prostaglandin --, therefor.

On the Page 2, in column 2, under "Other Publications", line 25, delete "Prostagladin" and insert -- Prostaglandin --, therefor.

On the Page 2, in column 2, under "Other Publications", line 46, delete "Retreived" and insert -- Retrieved --, therefor.

In the Specification

In column 2, line 22, delete "and and" and insert -- and --, therefor.

In column 3, line 5 (Table 1), delete "US P" and insert -- USP --, therefor.

In column 3, line 9 (Table 1), delete "US P" and insert -- USP --, therefor.

In column 3, line 11 (Table 1), delete "US P" and insert -- USP --, therefor.

In column 3, line 13 (Table 1), delete "US P" and insert -- USP --, therefor.

In column 3, line 15 (Table 1), delete "US P" and insert -- USP --, therefor.

In column 3, line 17 (Table 1), delete "US P" and insert -- USP --, therefor.

In column 3, line 32, delete "1OP" and insert -- IOP --, therefor.

In the Claims

In column 4, line 22, in claim 3, delete "solution" and insert -- composition --, therefor.

Signed and Sealed this
Seventeenth Day of November, 2015

Michelle K. Lee
*Director of the United States Patent and Trademark Office*